(12) United States Patent
Fournie et al.

(10) Patent No.: US 6,878,130 B2
(45) Date of Patent: Apr. 12, 2005

(54) EXTERNAL INFLATION INDICATOR FOR A LOW PROFILE GASTROSTOMY TUBE

(75) Inventors: Glenn G. Fournie, Smithton, IL (US); Mitchell Babkes, Maryland Heights, MO (US)

(73) Assignee: Sherwood Services AG, Schaffhausen (CH)

( * ) Notice: Subject to any disclaimer, the term of this patent is extended or adjusted under 35 U.S.C. 154(b) by 96 days.

(21) Appl. No.: 10/156,413

(22) Filed: May 28, 2002

(65) Prior Publication Data

US 2003/0225376 A1 Dec. 4, 2003

(51) Int. Cl.[7] .......................... A61M 29/00; A61M 5/32
(52) U.S. Cl. ............................. 604/100.01; 604/100.02; 604/175
(58) Field of Search ..................... 604/96.01, 97.03, 604/99.02, 99.03, 920, 175, 100.01, 100.02, 104–106; 606/194–196

(56) References Cited

U.S. PATENT DOCUMENTS

| | | | | |
|---|---|---|---|---|
| 4,016,885 A | * | 4/1977 | Bruner ................... | 604/100.01 |
| 4,134,407 A | * | 1/1979 | Elam .......................... | 604/920 |
| 4,398,542 A | | 8/1983 | Cunningham et al. ...... | 128/675 |
| 4,592,747 A | * | 6/1986 | Pool .......................... | 604/246 |
| 4,872,483 A | | 10/1989 | Shah .......................... | 137/557 |
| 5,218,970 A | | 6/1993 | Turnbull et al. ............ | 128/748 |
| 5,324,262 A | * | 6/1994 | Fischell et al. ........... | 604/99.04 |
| 5,342,321 A | | 8/1994 | Potter ......................... | 604/174 |
| 5,462,561 A | * | 10/1995 | Voda .......................... | 606/144 |
| 5,997,546 A | | 12/1999 | Foster et al. ............... | 606/108 |
| 6,530,898 B1 | * | 3/2003 | Nimkar et al. ........... | 604/97.03 |

* cited by examiner

Primary Examiner—Nicholas D. Lucchesi
Assistant Examiner—Matthew F DeSanto

(57) ABSTRACT

A gastrostomy device having an external inflationary indicator is disclosed which comprises an external retention member having a tubular member extending therefrom for providing a fluid pathway to a patient's gastrointestinal tract. The external retention member includes a fluid conduit in communication with a inflationary lumen for providing fluid to inflate a balloon member attached to the tubular member. The inflationary indicator includes a thin wall section of the external retention member which forms a flexible membrane that defines first and second portions divided by a separating bar. The flexible membrane assumes a convex shape when the balloon member is in an inflated condition, while it assumes a concave shape when in the deflated condition. The shape in shape of the flexible membrane provides the user with a visual and tactile indication as to the inflationary state of the balloon member.

12 Claims, 5 Drawing Sheets

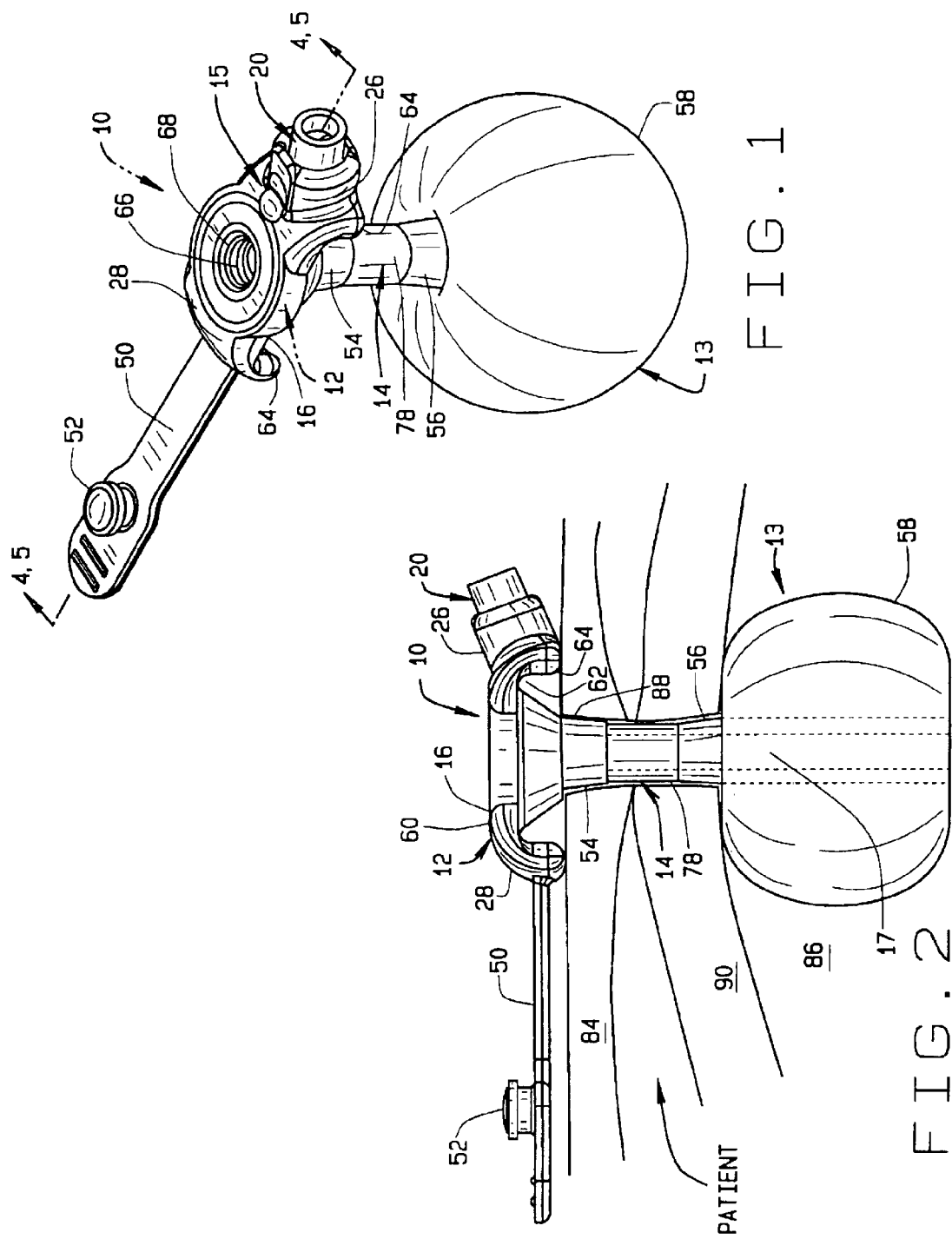

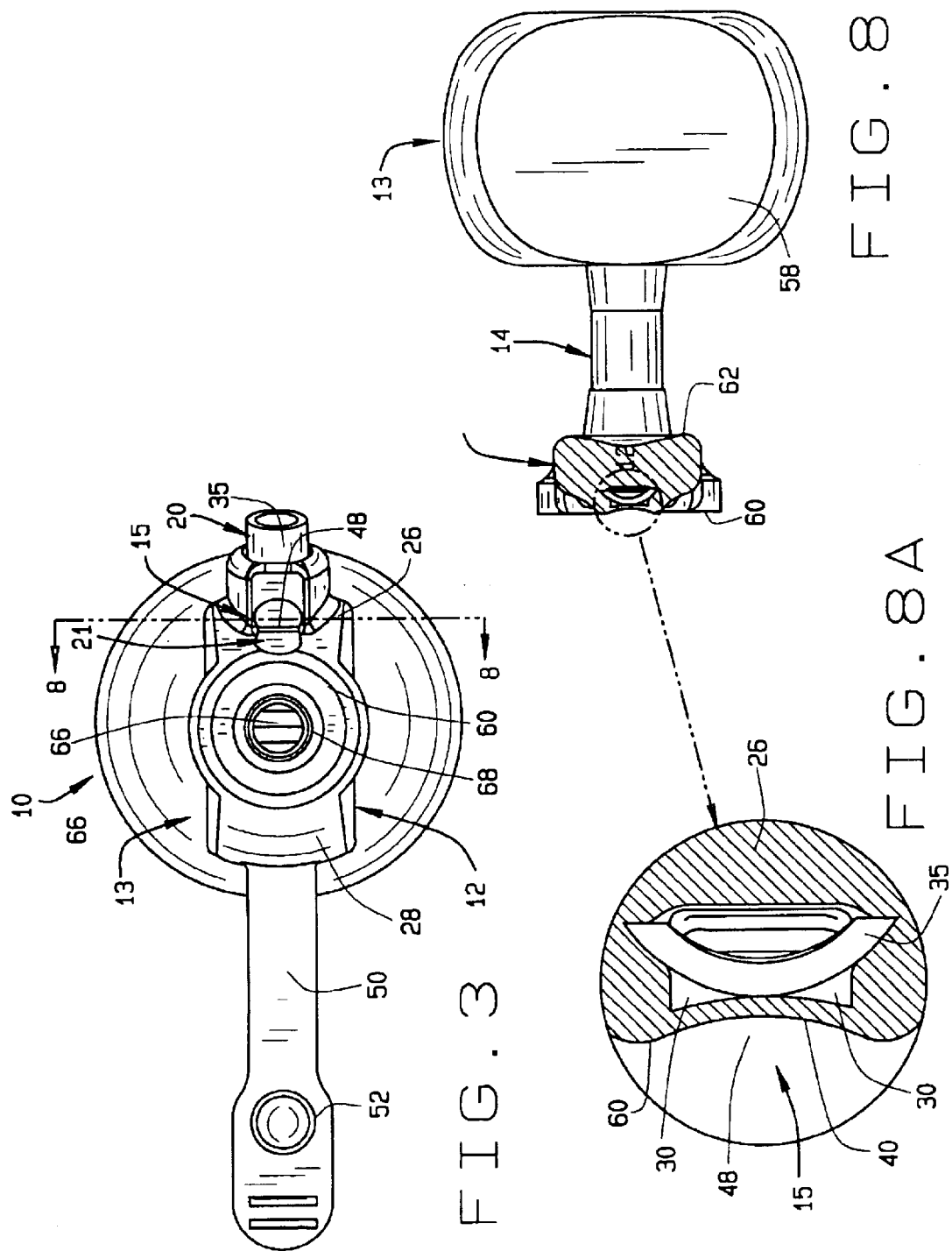

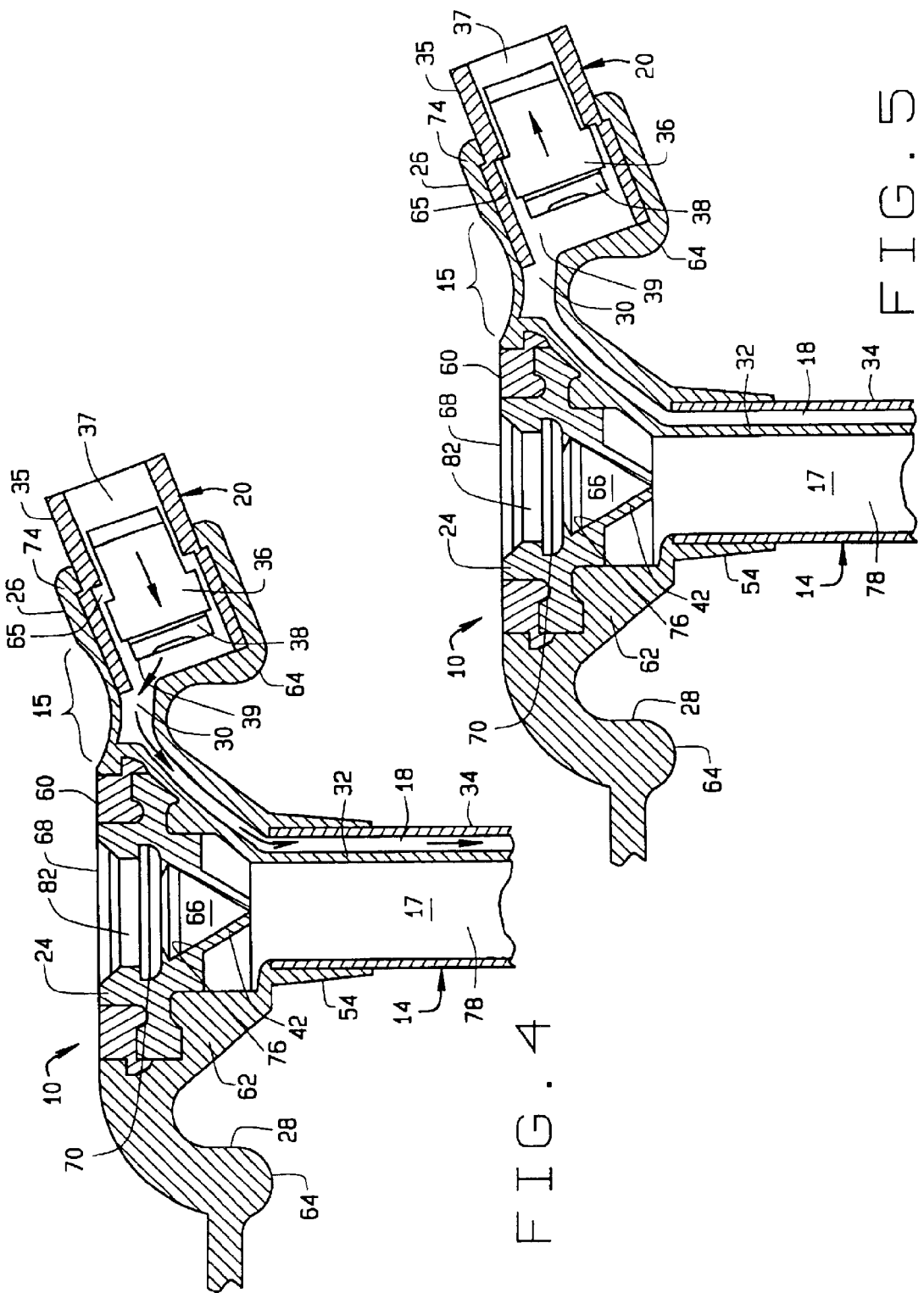

EXTERNAL INFLATION INDICATOR FOR A LOW PROFILE GASTROSTOMY TUBE

BACKGROUND OF THE INVENTION

1. Field of the Invention

The present invention relates to gastrointestinal feeding system, and more particularly to low profile gastrostomy devices having an inflatable balloon member. More specifically, the present invention relates to a low profile gastrostomy device having an indicator for indicating the inflationary state of the balloon member.

2. Prior Art

Low profile gastrointestinal feeding systems are frequently used for patients who are unable to take nutrition orally and require some type of gastrostomy device to provide nutrition through the gastrointestinal tract, such as the stomach. These gastrointestinal systems usually comprise a conventional feeding set of tubing attached to a source of nutrition at one end and a low profile gastrostomy device at the other end. The low profile gastrostomy device comprises an external retention member having a hollow tubular member extending axially therefrom with an inflatable balloon member attached to the tubular member. The tubular member provides a fluid pathway from the feeding set directly to the patient's gastrointestinal tract. The low profile gastrostomy device is normally inserted through a stoma formed through the patient's abdominal and stomach walls such that the balloon member enters the patient's gastrointestinal tract in a deflated condition and may be retained therein by placing the balloon member in an inflated condition and anchoring it against the wall of the gastrointestinal tract. Specifically, the balloon member is provided along a portion of the tubular member to hold and affix a portion of the gastrointestinal tract, i.e. the stomach, against the posterior abdominal wall of the patient when the balloon member is placed in the inflated condition. The stomach is so affixed by capturing the organ wall and abdominal wall between the inflated balloon member secured inside the organ and the external retention member seated on the outer abdominal wall of the patient.

As noted above, to anchor the low profile gastrostomy device after deployment inside the patient, the inflatable balloon member is placed in the inflated condition by a user which prevents it from being withdrawn through the stoma of the patient. Once the low profile gastrostomy device is so deployed, it is often desirable for the user to have some indication as to the inflationary state of the inflatable balloon, especially if a leak develops or fluid is inadvertently evacuated. U.S. Pat. No. 4,592,747 to Pool discloses a flow sensor having a body that defines a recessed surface covered by a flexible cover for medical dispensing systems. The flexible cover is movable between a contracted position wherein the cover contacts the recessed surface in response to changes in fluid flow through an internal passage. Although the Pool device provides an indication of fluid flow through a conduit, the flow sensor does not give a clear visual indication as to the inflatable condition of a flexible membrane, such as a balloon. Moreover, the cover of the flow sensor is not integral and must be securely engaged to the flow sensor body in order to ensure proper operation.

Similarly, U.S. Pat. No. 4,398,542 to Cunningham et al. discloses a fluid pressure measurement device comprising a body having an opening through an exterior surface into the channel with a separate flexible membrane covering the opening which is sealed to the body. The flexible membrane is also movable to an expanded position in response to a positive pressure being carried by IV tubes. However, similar to the Pool device, the flexible membrane is not integral and may be difficult to view properly in the dark or dim lighting conditions.

Other devices such as U.S. Pat. No. 4,872,483 to Shah and U.S. Pat. No. 5,218,970 to Turnball et al. employ electronic devices for indicating the inflationary state of a flexible balloon member, such as a pressure cuff monitor or electronic manometer. Unfortunately, these electronic devices are expensive to manufacture and require mechanical assemblies to provide a visual indication of inflationary state. Unfortunately, prior art gastrostomy devices do not have simple and inexpensive means for visually and tactilely indicating the inflationary state of a balloon member.

Therefore, there appears a need in the art for an integral external inflationary indicator for a low profile gastrostomy device that provides a continuous visual and tactile indication relating to the inflationary state of the balloon member.

OBJECTS AND SUMMARY OF THE INVENTION

Accordingly, the primary feature of the present invention is to provide an indicator that gives a continuous visual indication as to the inflationary state of the balloon member.

Another feature is to provide a gastrostomy device having an indicator that gives a continuous tactile indication as to the inflationary state of the balloon member.

Yet, a further feature is to provide an indicator that gives both visual and tactile indications of inflationary state of the balloon member.

A further feature is to provide an external indicator that is integral with the body of the gastrostomy device.

Another further feature is to provide an indicator that provides a visual indication of the inflationary condition of the balloon member after the gastrostomy device has been deployed inside a patient and the balloon member hidden from view.

Yet another feature is to provide an indicator that gives an indication of inflationary condition by a change in shape or configuration of a separating bar.

These and other objects of the present invention are realized in the preferred embodiment of the present invention, described by way of example and not by way of limitation, which provides for an external inflationary indicator for a gastrostomy device.

In brief summary, the present invention overcomes and substantially alleviates the deficiencies in the prior art by providing a gastrostomy device comprising an external retention member having a body adapted for seating against a patient's body. The body defines an inflationary lumen and a fluid lumen disposed axially therein that extend through a hollow tubular member having one end attached to the external retention member. The other end of the tubular member defines an opening in communication with the fluid lumen for supplying fluid to a patient's gastrointestinal tract, while the inflationary lumen extends along the outer surface of the tubular member and communicates with an inflatable balloon member which is attached to a portion of the tubular member. The balloon member is movable between a first deflated condition and a second inflated condition when inserting and anchoring the balloon member inside a patient's gastrointestinal tract during deployment of the gastrostomy device. The gastrostomy device further comprises an external indicator that forms an integral part of the external retention member and provides a visual and tactile indication to a user as to the inflationary state of the balloon member. The external indicator is defined by a thin wall section formed along a portion of the external retention member formed adjacent a fluid conduit defined therein. The fluid conduit communicates with a one-way valve disposed along one side of the external retention member and provides a means for supplying fluid to inflate the balloon member.

In accordance with one aspect of the present invention, the external indicator provides a continuous visual indication to the user as to the inflationary state of the balloon member. The thin wall section of the external indicator includes a flexible membrane having first portion and a second portion divided by a separating bar. Preferably, the separating bar is configured such that the bar divides into two parts and visually separates as the balloon member becomes fully inflated. Further, first and second portions form a generally bubble-like configuration that changes shape relative to the inflationary state of the balloon member. When the balloon member is in the deflated condition, first and second portions form a generally concave shape, while in the inflated condition first and second portions form a generally convex shape. The changing shape of the first and second portions also provides the user a continuous tactile indication as to the inflationary state of the balloon member based on the particular configuration of the external indicator.

Additional objects, advantages and novel features of the invention will be set forth in the description which follows, and will become apparent to those skilled in the art upon examination of the following more detailed description and drawings in which like elements of the invention are similarly numbered throughout.

BRIEF DESCRIPTION OF THE DRAWINGS

FIG. 1 is a perspective view of the gastrostomy device according to the present invention;

FIG. 2 is a side view of the gastrostomy device shown anchored against the posterior abdominal wall of a patient according to the present invention;

FIG. 3 is a top view of the gastrostomy device according to the present invention;

FIG. 4 is a cross sectional view of the gastrostomy device taken along line 4—4 of FIG. 1 showing the valve in the open position according to the present invention;

FIG. 5 is a cross sectional view of the gastrostomy device taken along line 5—5 of FIG. 1 showing the valve in the closed position according to the present invention;

FIG. 8 is a cross-sectional view of the external retention member taken along line 8—8 of FIG. 3 according to the present invention;

FIG. 8a is an enlarged sectional view of the external retention member showing the external inflationary indicator according to the present invention;

DETAILED DESCRIPTION OF THE INVENTION

Figure 6:
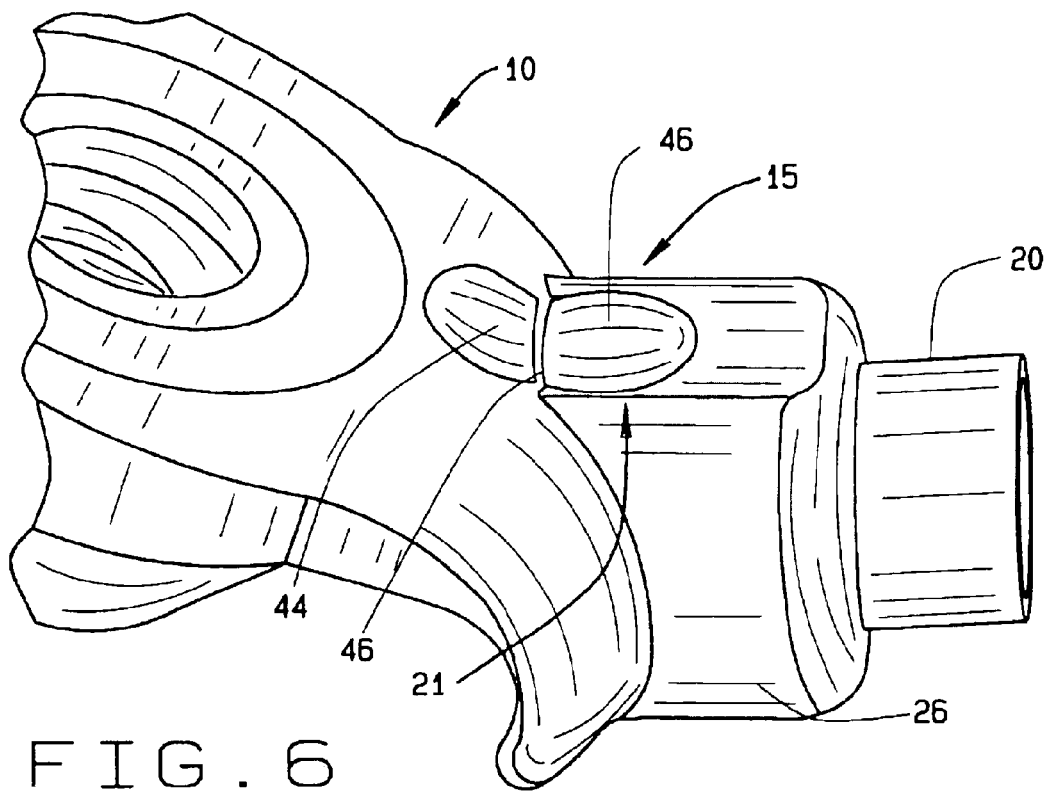
FIG. 6 is a perspective view of the gastrostomy device showing the external inflationary indicator in the first position according to the present invention.

Referring to the drawings, the preferred embodiment of the external inflationary indicator for a gastrostomy device 10 of the present invention is illustrated and generally indicated as 15 in FIG. 1. The gastrostomy device 10 comprises an external retention member 12 attached to a fluid administration system (not shown) adapted to be seated on the outer abdominal wall 84 or other suitable portion of a patient for retaining device 10 thereon and providing fluids directly to the patient's gastrointestinal tract 86. The external retention member 12 is attached or integral with a hollow tubular member 14 that is inserted through a stoma 88 formed by a gastropexy of the stomach wall 90 and abdominal wall 86. Tubular member 14 provides a conduit for supplying fluid directly to the gastrointestinal tract 86 or jejunum (not shown) of patient. An inflatable balloon member 13 is provided along the lower portion of tubular member 14 for retaining the gastrostomy device 10 inside a patient's gastrointestinal tract 86 after deployment.

Referring to FIGS. 1 and 2, the external retention member 12 includes a body 16 comprising a top surface 60 and a bottom surface 62. The bottom surface 62 forms opposing legs 64 adapted to be seated against the outer abdominal wall 84 of a patient and to also serve to retain the external retention member 12 thereto when the tubular member 14 is inserted through the stoma 88 of the patient. The top surface 60 of external retention member 12 defines an opening 68 which communicates with a primary lumen 66 (FIGS. 4 and 5) extending axially through body 16 for supplying fluid to the patient through tubular member 14. Primary lumen 66 includes an area 82 (FIG. 4) configured for snap fit engagement with an insert 76 that includes a valve portion 42 for preventing reflux of fluid back through gastrostomy device 10. Preferably, valve portion 42 is a duck bill valve, or in the alternative, a slit valve that permits fluid flow in one direction.

As illustrated in FIGS. 1, 2, 4 and 5, tubular member 14 includes upper and lower cuffs 54, 56 which attach tubular member 14 to external retention member 12 and balloon member 13, respectively. However, the present invention contemplates that the tubular member 14 may be made integral with both external retention member 12 and balloon member 13. Tubular member 14 defines a fluid lumen 17 which provides a conduit for providing fluid to a patient's gastrointestinal area. Fluid lumen 17 communicates with primary lumen 66 of external retention member 12 through valve portion 42. Referring to FIG. 2, tubular member 14 has a hollow elongated body 78 (shown in partial phantom) defining fluid lumen 17 which communicates with an opening 80 formed at the distal end of elongated body 78. The inflatable balloon member 13 provides a means for retaining the gastrostomy device 10 after deployment inside the patient and is attached to the lower portion of tubular member 14 by conventional bonding methods known in the art. To inflate balloon member 13, an inflationary lumen 18 is also formed through elongated body 78 which extends axially through tubular member 14 between inner and outer walls 32 and 34 in parallel relationship with fluid lumen 17. Inflationary lumen 18 is in fluid communication with fluid conduit 30 and the interior of balloon member 13.

As shown, external retention member 12 further comprises a first extension 26 and second extension 28 formed on opposite sides of body 16. First extension 26 extends outwardly from leg 64 to form a receptacle 74 (FIG. 5) for securely receiving a valve 20 therein, while second extension 28 includes a tether 50 defining a retention cap 52 at the free end thereof. The retention cap 52 is adapted to securely engage undercut 70 defined along space 82 of external retention member 12 when manually sealing off opening 68 to fluid flow communication.

Referring to FIGS. 4 and 5, receptacle 74 communicates with fluid conduit 30 which provides a pathway for the flow of fluid when either inflating or deflating balloon member 13 through valve 20. Valve 20 provides a means for inflating balloon member 13 through inflationary lumen 18. In assembly, valve 20 comprises a valve body 35 defining a chamber 65 in selective communication with distal and proximal openings 37 and 39 formed at opposite ends of chamber 65. Valve body 35 further includes an activation rod 36 disposed inside chamber 65 that is operatively associated with a valve seat 38 for selectively permitting or preventing fluid flow through valve body 35 when properly actuated. To inflate balloon member 13, the user engages the tip of a syringe (not shown) with valve body 35 such that activation rod 36 moves and causes valve seat 38 to unseat and permit discharged fluid from the syringe to enter fluid conduit 30 through proximal opening 39. As illustrated specifically in FIG. 4, discharged fluid travels from fluid conduit 30 through inflationary lumen 18 and enters the interior portion of balloon body 58 causing it to expand to a diameter greater than the diameter of tubular member 14.

Figure 7:
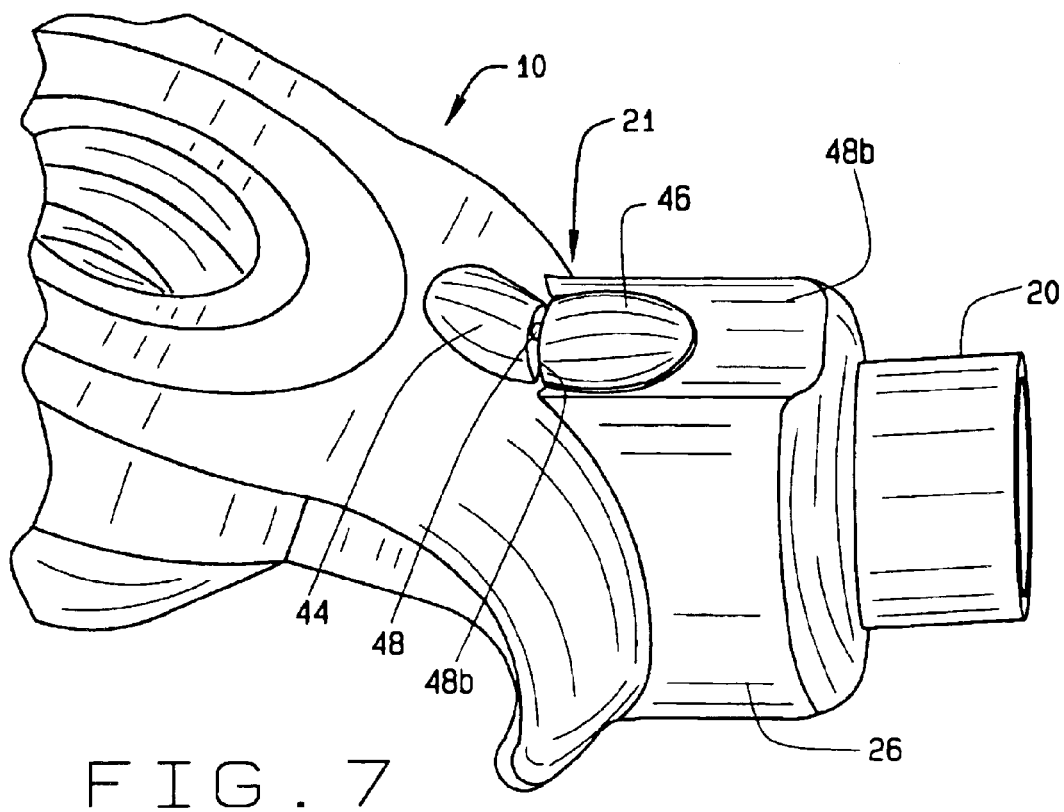
FIG. 7 is a perspective view of the gastrostomy device showing the external inflationary indicator in the second position according to the present invention.

Referring to FIGS. 6 and 7, the inflationary indicator 15 according to the present invention shall now be discussed in greater detail. Inflationary indicator 15 provides a continuous visual and tactile indication to the user of the inflationary state of balloon member 13. Preferably, inflationary indicator 15 comprises a pliable and flexible membrane 21 along the exterior portion of external retention member 12 adjacent fluid conduit 30. Flexible membrane 21 includes a first portion 44 and second portion 46 divided by a separating bar 48. Preferably, separating bar 48 comprises a first bar 48a formed proximate a second bar 48b that provides a distinctive visual marker between first and second portions 44 and 46.

According to one aspect of the present invention, the presence or absence of fluid inside fluid conduit 30 causes the first and second portions 44 and 46 to assume different and distinctive shapes. When balloon member 13 assumes an inflated condition as illustrated in FIG. 6, fluid conduit 30 fills with fluid which applies a pressure against thin wall section 40 and causes first and second portions 44 and 46 to assume a generally convex shape, while placing the balloon member 13 in the deflated condition causes portions 44 and 46 to assume a generally concave shape as fluid is evacuated back through fluid conduit 30 which releases the internal pressure applied by the fluid to thin wall section 40 that defines flexible membrane 21. In this manner, a user can visually confirm whether balloon member 13 is either in the deflated or inflated condition by simply viewing the shape of the flexible membrane 21 and configuration of the separating bar 48. Further, the user need only feel the shape of the flexible membrane 21 to determine the inflationary state of balloon member 13. For example, the concave shape of flexible membrane 21 provides a recessed feel to the user which indicates a deflated condition, while the convex shape provides a bumpy feel to the user that indicates an inflated condition.

Figure 9A:
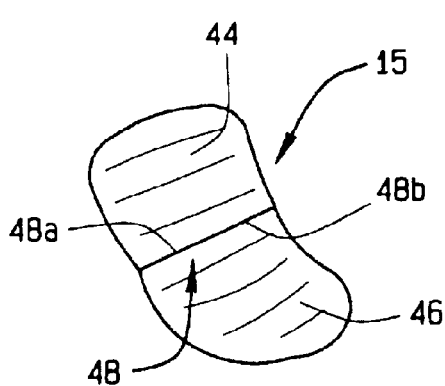
FIG. 9a is an isolated view of a preferred embodiment of the flexible membrane in the deflated condition according to the present invention.
Figure 9B:
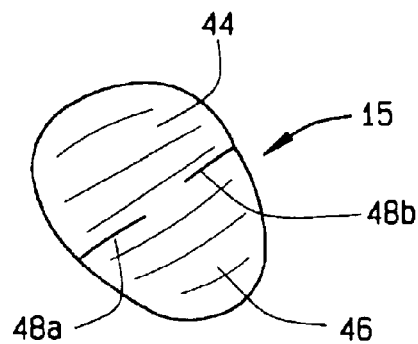
FIG. 9b is an isolated view of the preferred embodiment of flexible membrane shown in the inflated condition according to the present invention.

According to another aspect of the present invention, the configuration of the separating bar 48 varies in response to the inflationary state of balloon member 13 which visually indicates the inflationary state to the user. As illustrated in FIGS. 4 and 7, fluid entering balloon member 13 causes flexible membrane 21 to assume a generally convex shape as fluid begins to fill fluid conduit 30 which applies an outward pressure against first and second portions 44 and 46 of flexible membrane 21. Fluid filling fluid conduit 30 forces thin wall portion 40 to bulge outwardly such that separating bar 48 appears to separate into two distinctive portions. Referring to the preferred embodiment illustrated in FIGS. 9a and 9b, separating bar 48 appears to separate into first and second bars 48a and 48b to the viewer as balloon member 13 assumes an inflated condition and flexible membrane 21 begins to noticeably bulge outward. However, when fluid is withdrawn from balloon member 13, the removal of fluid from fluid conduit 30 causes flexible membrane 21 to assume a generally concave shape as thin wall section 40 is caused to bulge inwardly. In this concave or bowl-like configuration, bars 48(a) and 48(b) appear to substantially reconnect into single separating bar 48, thereby giving a visual indication that balloon member 13 is in the deflated condition.

Figure 10A:
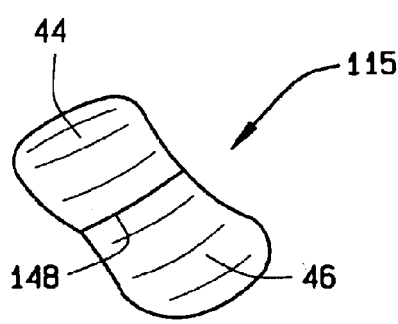
FIG. 10a is an isolated view of an alternate embodiment of the flexible membrane shown in the deflated condition according to the present invention.
Figure 10B:
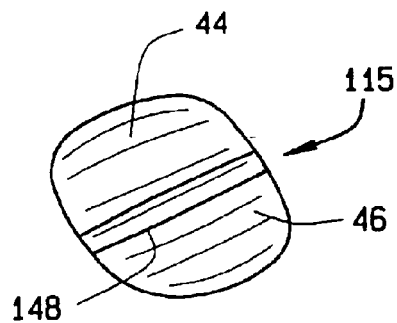
FIG. 10b is an isolated view of the alternate embodiment of the flexible membrane shown in the inflated condition according to the present invention.

In accordance with another aspect of the present invention an alternate embodiment 115 of the external inflationary indicator is shown in FIGS. 10a and 10b. Inflationary indicator 115 comprises a marking line 148, rather than a separating bar 48, that divides first and second portions 44 and 46. As balloon member 13 assumes an inflated condition marking line 148 assumes a greater thickness, while in the deflated condition marking line assumes a thinner configuration.

Figure 11A:
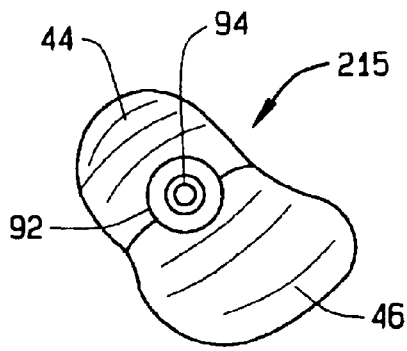
FIG. 11a is an isolated view of another alternate embodiment of the flexible membrane shown in the deflated condition according to the present invention.
Figure 11B:
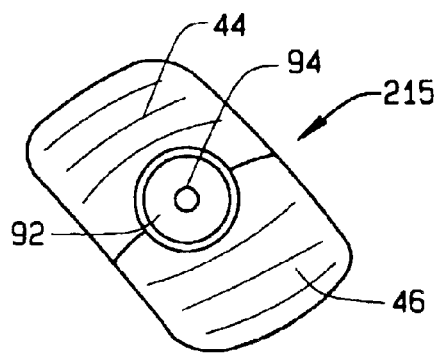
FIG. 11b is an isolated view of the alternate embodiment of the flexible membrane shown in the inflated condition according to the present invention.

In accordance with another aspect of the present invention alternate embodiment 215 of the external inflationary indicator is illustrated in FIGS. 11a and 11b. Inflationary indicator 215 comprises a dot 94 surrounded by a circle 92. In operation, when balloon member 13 assumes an inflated condition inflationary indicator 215 changes shape such that circle 92 is visible and concentrically surrounds dot 94, while in the deflated condition circle 92 appears to merge with said dot 94.

Preferably, flexible membrane 21 is made from silicone, although the present invention contemplates that other suitable pliable medical-grade materials may be used without departing from the spirit and scope of the present invention.

In accordance with another aspect of the present invention, inflationary indicators 15, 115 and 215 may have different color schemes in order to permit the user to better distinguish the indicators 15, 115 and 215 from the rest of low profile gastrostomy device 10.

Although particular embodiments of the invention have been shown, it is not intended that the invention be limited thereby, instead, it is not intended that the present invention is intended to be limited by only the appended claims.

We claim:

1. A gastrostomy device comprising:
   an external retention member having a body, said body defining an inflationary lumen and a fluid lumen, said body further defining an indicator, said indicator including first and second portions, a hollow tubular member, one end of said hollow tubular member being attached to said external retention member and in communication with said fluid lumen, while another end of said hollow tubular member defines an opening in communication with said fluid lumen, said inflationary lumen extending along said hollow tubular member, an inflatable balloon member attached to said hollow tubular member and in communication with said inflationary lumen, said inflatable balloon member being operable between a first inflated condition and a second deflated condition, wherein said first and second portions of said indicator assume a convex shape indicating that said inflatable balloon member is in said first inflated condition, wherein said indicator includes a marker to provide a visual indication of whether said inflatable balloon member is in said first inflated condition or said second deflated condition, and wherein said indicator provides a tactile indication of whether said inflatable balloon member is in said first inflated condition or said second deflated condition based on whether said indicator has assumed said convex shape.

2. The gastrostomy device according to claim 1, wherein external retention member includes a valve, said valve being in selective communication with said inflationary lumen.

3. The gastrostomy device according to claim 2, wherein said body defines a receptacle for housing said valve.

4. The gastrostomy device according to claim 3, wherein said receptacle communicates with a fluid conduit, said fluid conduit being in communication with said inflationary lumen and said valve.

5. The gastrostomy device according to claim 4, wherein said fluid conduit is formed adjacent said indicator.

6. The gastrostomy device according to claim 2, wherein said valve is a one-way valve.

7. The gastrostomy device according to claim 2, wherein said valve is adapted to engage a syringe.

8. The gastrostomy device according to claim 2, wherein said valve is adapted to selectively provide fluid to said inflatable balloon member through said inflationary lumen.

9. The gastrostomy device according to claim 1, wherein said indicator is located along a thin wall section of said body.

10. A gastrostomy device comprising:

an external retention member having a body, said body defining an inflationary lumen in communication with a fluid conduit, said body further defining an indicator, said indicator including first and second portions operably associated with said fluid conduit, a hollow tubular member, one portion of said hollow tubular member is attached to said external retention member while the other portion defines an opening, said inflationary lumen extending along said hollow tubular member, an inflatable balloon member attached to said other portion of said hollow tubular member, said inflatable balloon member being in communication with said inflationary lumen and operable between an inflated condition and a deflated condition, said indicator further comprising a bar for providing said visual indication, wherein said indicator provides a visual indication on whether the inflatable balloon member is in said inflated condition or said deflated condition such that said bar separates into first and second bars when said inflatable balloon member is placed in said inflated condition, and said first and second bars appear to substantially reattach when said inflatable balloon member is placed in the deflated condition, wherein said first and second bars provide a tactile indication of a change in inflationary state of said inflatable balloon member based on whether said first and second portions assume a convex shape indicating that said inflatable balloon member is in said inflated condition.

11. A gastrostomy device comprising:

an external retention member having a body, said body defining an inflationary lumen in communication with a fluid conduit, said body further defining an indicator, said indicator being operably associated with said fluid conduit, a hollow tubular member, one portion of said tubular member being attached to said external retention member while the other portion defines an opening, said inflationary lumen extending along said tubular member, an inflatable balloon member attached to said other portion of said tubular member, said inflatable balloon member being in communication with said inflationary lumen and being operable between an inflated condition and a deflated condition, wherein said indicator further comprises a marking line said marking line assuming a greater thickness when said inflatable balloon member is placed in the inflated condition and said marking line assuming a lesser thickness when said inflatable balloon member is placed in the deflated condition.

12. A gastrostomy device comprising:

an external retention member having a body, said body defining an inflationary lumen in communication with a fluid conduit, said body further defining an indicator, said indicator being operably associated with said fluid conduit, a hollow tubular member, one portion of said tubular member being attached to said external retention member while the other portion defines an opening, said inflationary lumen extending along said tubular member, an inflatable balloon member attached to said other portion of said tubular member, said inflatable balloon member being in communication with said inflationary lumen and being operable between an inflated condition and a deflated condition, said indicator comprising a circle surrounding a dot, wherein said dot and said circle appear to merge together when said inflatable balloon member is placed in the deflated condition, while said circle is visible and concentrically surrounds said dot when said inflatable balloon member is placed in the inflated condition.

* * * * *